(12) United States Patent
Grossschmidt et al.

(10) Patent No.: US 8,506,924 B2
(45) Date of Patent: Aug. 13, 2013

(54) PROCESS AND APPARATUS FOR PREPARING ACETYLENE AND SYNTHESIS GAS

(75) Inventors: Dirk Grossschmidt, Mannheim (DE); Michael Russ, Roemerberg (DE); Peter Renze, Mannheim (DE); Maximilian Vicari, Limburgerhof (DE); Christian Weichert, Bad Duerkheim (DE); Kai Rainer Ehrhardt, Speyer (DE); Horst Neuhauser, Dudenhofen (DE); Hans Zapf, Mutterstadt (DE); Michael L. Hayes, Gonzales, LA (US)

(73) Assignee: BASF SE, Ludwigshafen (DE)

( * ) Notice: Subject to any disclaimer, the term of this patent is extended or adjusted under 35 U.S.C. 154(b) by 35 days.

(21) Appl. No.: 13/292,777

(22) Filed: Nov. 9, 2011

(65) Prior Publication Data

US 2012/0119150 A1    May 17, 2012

Related U.S. Application Data

(60) Provisional application No. 61/412,415, filed on Nov. 11, 2010.

(51) Int. Cl.
 *C01B 3/24* (2006.01)
 *C01B 3/38* (2006.01)
(52) U.S. Cl.
 USPC .......................................... 423/650; 252/373
(58) Field of Classification Search
 USPC ........................................................ 252/373
 See application file for complete search history.

(56) References Cited

U.S. PATENT DOCUMENTS

| 2,672,488 | A | 3/1954 | Jones |
| 3,240,836 | A | 3/1966 | Pechtold et al. |
| 5,789,644 | A | 8/1998 | Pässler et al. |
| 2011/0305605 | A1 | 12/2011 | Jaeger et al. |

FOREIGN PATENT DOCUMENTS

| DE | 875 198 | 4/1953 |
| DE | 1 051 845 | 3/1959 |
| DE | 1 057 094 | 5/1959 |
| DE | 1 148 229 | 5/1963 |
| DE | 1 250 424 | 9/1967 |
| DE | 2 007 997 | 9/1970 |

(Continued)

OTHER PUBLICATIONS

"Ullmann's Encyclopedia of Industrial Chemistry", Fifth, Completely Revised Edition, vol. A1: Abrasives to Aluminum Oxide, 50 pages.

(Continued)

*Primary Examiner* — Melvin C. Mayes
*Assistant Examiner* — Kenneth Vaden
(74) *Attorney, Agent, or Firm* — Oblon, Spivak, McClelland, Maier & Neustadt, L.L.P.

(57) ABSTRACT

A process for preparing acetylene and synthesis gas by partial oxidation of hydrocarbons with oxygen, by first separately preheating the hydrocarbon gas and oxygen gas, and then reacting the gases and cooling the products rapidly. The reactor wall is blanketed with a purge gas stream, introduced through a plurality of feed lines. These feed lines deliver purge gas in a vector direction within a 10° angle of the main flow direction of the reactive gas stream. The purge gas is delivered at multiple stages relative to the main flow direction of the reactive gas stream, and the free cross section of the firing space available to the reactive gas stream, at the height of the feed lines of the purge gas stream, is approximately constant.

12 Claims, 4 Drawing Sheets

(56) References Cited

FOREIGN PATENT DOCUMENTS

| | | |
|---|---|---|
| DE | 2 307 300 | 8/1973 |
| DE | 39 04 330 A1 | 8/1990 |
| DE | 44 22 815 A1 | 1/1996 |
| WO | WO 2010/097300 A1 | 9/2010 |
| WO | WO 2011/073123 A2 | 6/2011 |

OTHER PUBLICATIONS

U.S. Appl. No. 13/292,691, filed Nov. 9, 2011, Russ, et al.
U.S. Appl. No. 61/412,406, filed Nov. 11, 2010, Russ, et al.
U.S. Appl. No. 61/365,802, filed Jul. 20, 2010, Koenigsmann, et al.
U.S. Appl. No. 13/183,683, filed Jul. 15, 2011, Koenigsmann, et al.
U.S. Appl. No. 61/411,931, filed Nov. 10, 2010, Renze, et al.
U.S. Appl. No. 61/389,287, filed Oct. 4, 2010, Renze, et al.
U.S. Appl. No. 13/251,647, filed Oct. 3, 2011, Renze, et al.
International Search Report issued Apr. 20, 2012 in Application No. PCT/EP2011/069697 (With English Translation of Category of Cited Documents).
U.S. Appl. No. 13/516,865, filed Jun. 18, 2012, Grossschmidt, et al.

PROCESS AND APPARATUS FOR PREPARING ACETYLENE AND SYNTHESIS GAS

The present application incorporates the provisional U.S. application No. 61/412,415 filed Nov. 11, 2010 by reference.

The present invention relates to an improved process for preparing acetylene and synthesis gas by partial oxidation of hydrocarbons in a reactor, in which a stream comprising the hydrocarbon and a stream comprising the oxygen are fed to the reactor, and to an apparatus for performing the process according to the invention.

High-temperature reactions for partial oxidation of hydrocarbons are typically performed in a reactor system composed of mixing unit, burner and quench unit.

One example of such a partial oxidation in the high-temperature range is the preparation of acetylene and synthesis gas by partial oxidation of hydrocarbons. This is described, for example, in DE 875198, DE 1051845, DE1057094 and DE 4422815.

These documents explain the mixer/burner block/firing space/quench combinations typically used for the BASF-Sachsse-Bartholome acetylene process—referred to hereinafter, when reference is being made to the combination, simply as "reactor".

In this process, the starting materials, for example natural gas and oxygen, are heated separately, typically up to 600° C. In a mixing zone, the reactants are mixed intensively and, after flowing through a burner block, reacted exothermically. In these cases, the burner block consists of a particular number of parallel channels in which the flow velocity of the ignitable oxygen/natural gas mixture is higher than the flame velocity (reaction rate, conversion rate), in order to prevent the flame from penetrating into the mixing space. The metallic burner block is cooled in order to withstand the thermal stresses. According to the residence time in the mixing space, the risk arises of premature ignition and reignition owing to the limited thermal stability of the mixtures. The term "ignition delay time" or "induction time" is used here as the period within which an ignitable mixture does not undergo any significant intrinsic thermal alteration. The induction time depends on the type of hydrocarbons used, the mixing state, pressure and temperature. It determines the maximum residence time of the reactants in the mixing space. Reactants such as hydrogen, liquefied gas or light petroleum, the use of which is particularly desirable owing to enhanced yield and/or capacity in the synthesis process, are notable for a comparatively high reactivity and hence short induction time.

The acetylene burners being used on the present production scale are notable for their cylindrical geometry in the firing space. The burner block preferably has hexagonally arranged passage bores. In one embodiment, for example, 127 bores of internal diameter 27 mm are arranged hexagonally on a circular base cross section with diameter approx. 500 mm. In general, the channel diameters used are of diameter about 19 to 27 mm. The downstream firing space in which the flame of the acetylene-forming partial oxidation reaction is stabilized is likewise of cylindrical cross section, is water-cooled and corresponds in terms of appearance to that of a short tube (for example of diameter 180 to 533 mm and of length 380 to 450 mm). At the height of the surface of the burner block on the firing space side, what is called auxiliary oxygen is supplied to the reaction space. This ensures flame stabilization and hence a defined distance of the flame root and hence of the commencement of reaction from the stoppage of reaction by the quench unit. The entire burner composed of burner block and firing space is hung from the top of a quench vessel of relatively large cross section by means of a flange. At the height of the exit plane from the firing space, outside the circumference thereof, quench nozzles are installed in one or more quench distributor rings, which atomize the quench medium, for example water or oil, with or without the aid of an atomization medium, and inject the reaction gases leaving the firing space approximately at right angles to the main flow direction. This direct quench has the task of cooling the reacting flow extremely rapidly to approx. 100° C. (water quench) and 200° C. (oil quench), such that further reactions, especially the degradation of acetylene formed, are frozen. The range and distribution of the quench jets is ideally such that a very substantially homogeneous thermal distribution is achieved within minimum time.

The acetylene burners used on the current production scale are notable for a cylindrical geometry of the firing space. The feedstocks are premixed by means of a diffuser and supplied, with avoidance of backmixing, to the burner block via passage bores in a hexagonal arrangement. In the known processes, the feedstocks are premixed in the mixing diffuser in a relatively large volume and with high preheating temperatures.

The industrial processes described form not only acetylene but essentially hydrogen, carbon monoxide and soot. The soot particles formed in the flame front can adhere as nuclei to the firing space side walls (firing space interior walls), which then results in the growth, deposition and baking-on of coke layers, which adversely affects the effectiveness of the process.

In the existing production processes with oil and water quenching, these deposits are periodically removed by mechanical cleaning in the region of the firing space interior walls by means of a stoker unit. For this purpose, complex control of the stoker unit is necessary (Ullmann's Encyclopedia of Industrial Chemistry, 5th Edition, Volume A1, pages 97-144) and, in addition, the particular use time of the mechanism is limited by the thermal stress in the combustion space.

There has been no lack of attempts to avoid the disadvantage of the baking of coke layers onto the firing space interior wall. For instance, the teaching of DE 2307300 discloses the injection of a gaseous substance into the reactor in a region between maximum temperature and quenching site (claim 1). This is intended to lead to reactions between the gases added and free radicals, which is intended to reduce coke formation (description, page 8, second paragraph).

DE 3904330 A1 describes a process for preparing acetylene black by thermal decomposition of acetylene. It is mentioned in this process, which differs significantly from the process for preparing acetylene (e.g. no partial oxidation), that an inert gas stream is optionally introduced.

DE 1148229 describes a process for operating pyrolysis chambers for treatment of hydrocarbons, wherein purging with steam is provided and cooling of the wall is supposed to lead to a water curtain (claim 1). No further information is given about the way in which the purging is executed. The process presented is not a partial oxidation (POx), the purge medium introduced is liquid water, and additional admixing of an oxidizing agent (e.g. oxygen) with the purge medium is not provided. Furthermore, a purge medium is injected only at a maximum of one site in the axial profile of the pyrolysis chamber.

According to the teaching of DE 1250424, a process for preparing acetylene is disclosed, in which steam is conducted along the interior wall. However, there is no further information about specific embodiments. Moreover, although multi-level feeding of a purge stream is disclosed in FIGS. 3 and 4, these solutions have a significant change in the free cross section of the combustion space over the height of the combustion chamber; viewed in flow direction of the product, a significant enlargement is observed here. This leads, however, to inhomogeneities in the reaction as a result of enhanced backmixing in the firing space, which impairs the effectiveness of the process. In addition, the purge medium according to this teaching, is superheated to 600-1000° C., which leads to significant problems in the material stability of the feed lines and to increased supply costs. This is additionally a different combustion concept of staged combustion with "cracked gas" injection (not conventional POx according to BASF-Sachse-Bartholome). According to the method, the fluid velocity of the purge exceeds the mean flue gas velocity in the reactor, which can lead to inhomogeneities in the boundary layer between the two flows and hence even to the suction of coke particles onto the firing space interior wall. According to this teaching, the firing space wall in process operation has a temperature of about 700° C., which can likewise lead to problems with material stability/selection.

DE 2007997 describes how an oil film on the interior wall of the reaction chamber is supposed to prevent coking (page 2, first paragraph). However, an oil film in a firing space tends to coking per se. Therefore, a hydrocarbon-containing (mineral) oil can be ruled out as a purge medium given the present challenge.

The processes disclosed in the documents cited for prevention or reduction of unwanted coke formation, however, are unsatisfactory with respect to effective use in the process for preparing acetylene. For instance, some of the documents, as explained, relate to other reactions where the conditions are quite different and there is no applicability. For instance, the partial oxidation in the process according to the invention is very demanding in terms of characteristics: the residence times play a particularly major role, the stoppage of the reaction must be very exact, and the addition of extraneous substances, including, for example, a purge gas or oxidizer, can move the reaction very rapidly with respect to the site and also the rate thereof, thus leading to a yield loss.

In addition, the prior art contains only general statements, often in terms of the problem to be solved, about the technical configuration.

In addition, no geometry specifications in terms of flow mechanics and reaction technology are presented, on the basis of which the purge medium could be minimized effectively and hence operating costs could be minimized and product yield optimized.

It is thus an object of the present invention to find an improved process for partial oxidation of hydrocarbons, which suppresses baked-on and deposited material on the firing space interior wall in a simple manner in terms of process technology, in order that there is no need for mechanical cleaning of these firing space interior walls, and hence for periodic removal by means of mechanical stoker units which are subjected to high thermal stress and are difficult to control.

Accordingly, a process has been found for preparing acetylene and synthesis gas by partial oxidation of hydrocarbons with oxygen, by first separately preheating the starting gases comprising a hydrocarbon-containing stream and an oxygen-containing stream and then mixing them in a mixing zone and, after they have flowed through the burner block, reacting them in the firing space and then cooling the products rapidly, wherein the firing space interior wall is blanketed with a purge gas stream, this purge gas stream is introduced by means of a plurality of feed lines and each of these feed lines is configured in the interior of the firing space such that the alignment of the direction vector of the main flow of the purge gas stream introduced deviates from the alignment of the direction vector of the main flow direction of the gas stream supplied through the burner block by an angle of not more than 10°, and the feed lines at the exit orifice thereof have an opening width of $1/1000$ to $3/100$, preferably $1/500$ to $1/100$, of the firing space diameter, there being a multi-level supply of the purge gas stream at successive points viewed in relation to the main flow direction of the gas stream supplied through the burner block, and the free cross section of the firing space which is available to the gas stream leaving the burner block for flow through the firing space at the height of the feed lines of the purge gas stream being approximately constant.

The process according to the invention can be applied to commonly known processes for preparing acetylene and/or synthesis gas by partial oxidation. Suitable feedstocks among the hydrocarbons preferably include alkanes, alkenes, natural gases, light petroleum, and mixtures thereof with, for example, $CO_2$, synthesis gas. The oxygen-containing stream can be supplied, for example, via oxygen, or else mixtures comprising oxygen and, for example, $CO_2$, $H_2O$, $N_2$ and/or noble gases.

Figure 1:
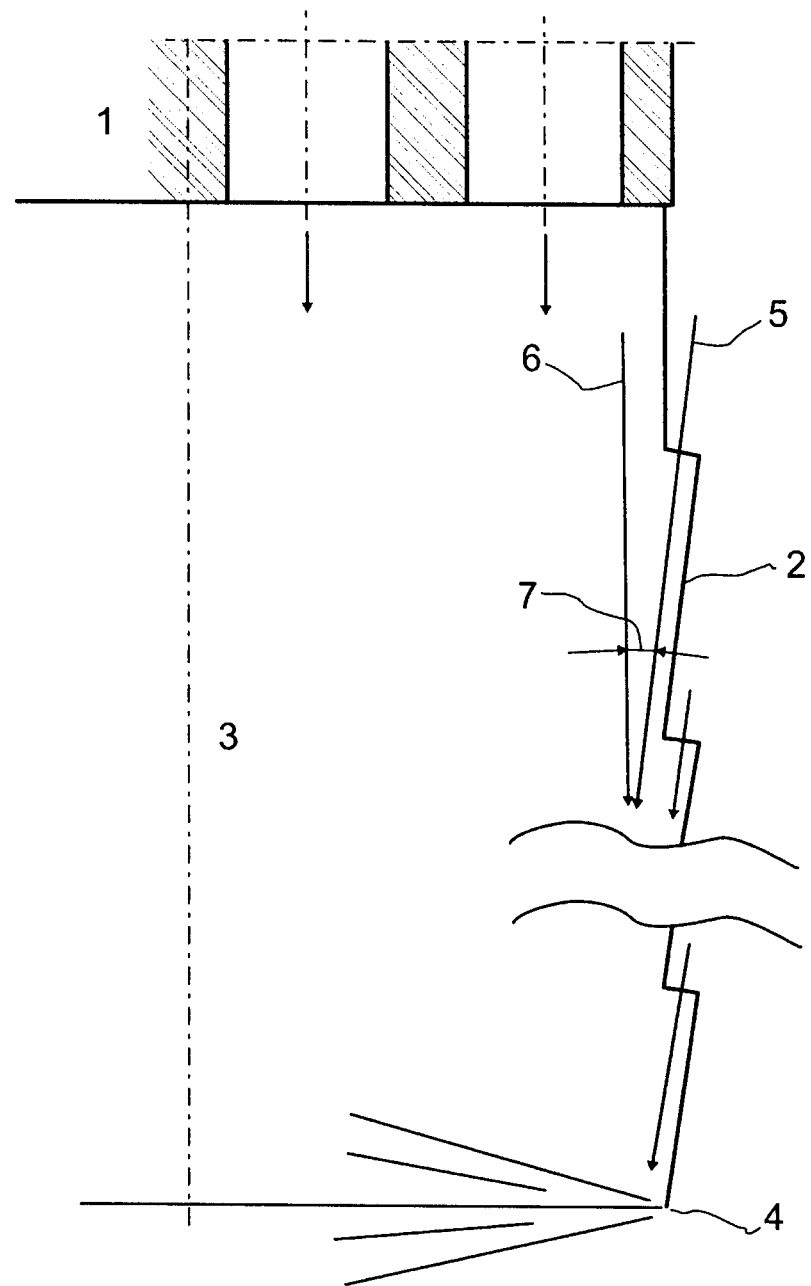
FIG. 1 is a schematic view showing detail of the inventive burner, in particular the interior wall of the firing space.

FIG. 1 shows a detail from the inventive burner. The firing space (3) in the context of the invention is understood to mean the tubular plant section (whose cross section may, for example, be circular, hexagonal or rectangular) downstream of the burner block (1) and upstream of the quench unit (4), which is bounded upstream on one side by the burner end surface with the exit holes of the burner block. Accordingly, the firing space interior wall (2) describes the interior surface—i.e. that facing the reaction volume—of this component, on which coking and growth of soot is to be avoided in accordance with the invention.

According to the invention, the purge gas stream used for this purpose is supplied via at least two feed lines as shown by way of example in FIG. 1. It is important in this context that the flow direction of the purge gas stream essentially corresponds to that of the added hydrocarbon or oxygen-containing stream. This is illustrated by way of example in FIG. 1: the feedstock stream flows through the firing space (3) in more or less vertical direction from the top downward. Even though deviations from this direction do of course exist at certain margins because of real effects, the main flow direction of this gas stream is thus aligned vertically downward, symbolized by the direction vector (6) (hereinafter "direction vector 1"). In general terms, "direction of main flow" in the context of this invention is understood to mean that flow direction through the component which develops in integral view above the boundary layer, which is pronounced in the vicinity of the wall. A feature essential to the invention is that the purge gas stream is preferably fed in such that the direction vectors of the main flow directions of purge gas stream (5) and the gas stream supplied through the burner block to the firing space are parallel. The direction vector of the purge stream (referred to hereinafter as "direction vector 2") also refers here to the main flow direction of the purge medium, reference being made to the above remarks regarding the term "main flow". The parallelism of these two direction vectors, which is essential to the invention, is ensured by arrangement of the surfaces of the exit orifices of the feed lines approximately at right angles to direction vector 1, preferably at right angles to this direction vector. As already mentioned, inhomogeneities which are observed in reality, unavoidable manufacturing tolerances and other phenomena may cause incomplete parallelism of the two main flows of the gas streams outlined (symbolized by direction vectors 1 and 2). However, even in the case of only approximate parallelism, the inventive positive effects can be observed to a significant degree; according to the invention, approximate parallelism preferably exists when the angle (7) between the two direction vectors 1 and 2 is less than a maximum of 10°, more preferably less than 5°; ideally, complete parallelism is ensured.

It is a significant aim of the process according to the invention to minimize the amount of the purge stream to be introduced in order to prevent premature reaction stoppage, which would reduce the acetylene yield. In addition, the amount of the purge medium used should be reduced for reasons of economic viability. At the same time, high effectiveness should be maintained here in the prevention of the coking of the wall of the firing space. In order to achieve this effect, a very substantially homogeneous purge film should be ensured over the entire firing space interior wall. One example of a design solution can be found in FIG. 2. This again shows a detail from an inventive apparatus, showing two different sections. In this effective design solution, the purge gas stream is fed into the firing space (2) through a plurality of feed lines (5) in the form of annular gaps, which are arranged successively in axial direction and preferably cover the entire firing space circumference. In order to ensure an amount of purge medium in homogeneous distribution over the firing space circumference in each of these annular gaps, each annular gap is fed by a plurality of feed tubes (4) in homogeneous distribution over the circumference from a distributor reservoir (3). Preferably, one to eight feed lines are advisable, which are distributed homogeneously over the circumference of the reactor. In addition, this figure shows some of the burner (1), the firing space interior wall (6) and a cooling jacket (7).

Preferably, the purge gas stream is supplied to the cylindrically shaped firing space in homogeneous distribution over the periphery in such a way that the purge gas stream is introduced with one to eight feed lines.

In this case, the exit orifices of the feed lines of one level ("feed level") may be arranged at the same height within the firing space. It may be particularly advisable to effect the feeding-in of the purge stream over the height of the firing space by means of a plurality of such feed levels as outlined above, the distance between the individual feed levels being 2 cm to 30 cm, more preferably 7 cm to 20 cm.

The exit orifices of the feed lines of the purge stream may preferably be circular, rectangular or square in shape, or form an annular gap surrounding the circumference of the firing space.

The feed lines of the purge gas stream (preferably annular gaps) have relatively small orifices. The opening width thereof is about $1/1000$ to $3/100$, preferably $1/500$ to $1/100$, of the firing space diameter. The firing space in the context of the invention is understood to mean the tubular plant section (whose cross section may, for example, be circular, hexagonal or rectangular) downstream of the burner block and upstream of the quench unit, which is bounded upstream on one side by the burner end surface with the exit holes of the burner block. Accordingly, the firing space diameter is understood to mean the greatest possible radial distance, or distance orthogonal to the firing space interior wall, which connects the firing space interior wall(s). When this distance is constant irrespective of the axial extent of the tubular firing space, reference may be made in the context of the invention to a constant firing space diameter. In general, the firing space diameters are, for instance, within a range from 10 to 2000 mm, preferably from 150 to 1000 mm. Opening width is understood in this context to mean the maximum radial dimension of an outlet of the purge medium into the firing space. In the case of a feed line with circular cross section, it is thus the circle diameter, and in the case of a particularly preferred annular gap the opening width. In general, the opening width is 0.2 to 10 mm, preferably 0.3 to 5 mm.

Figure 2:
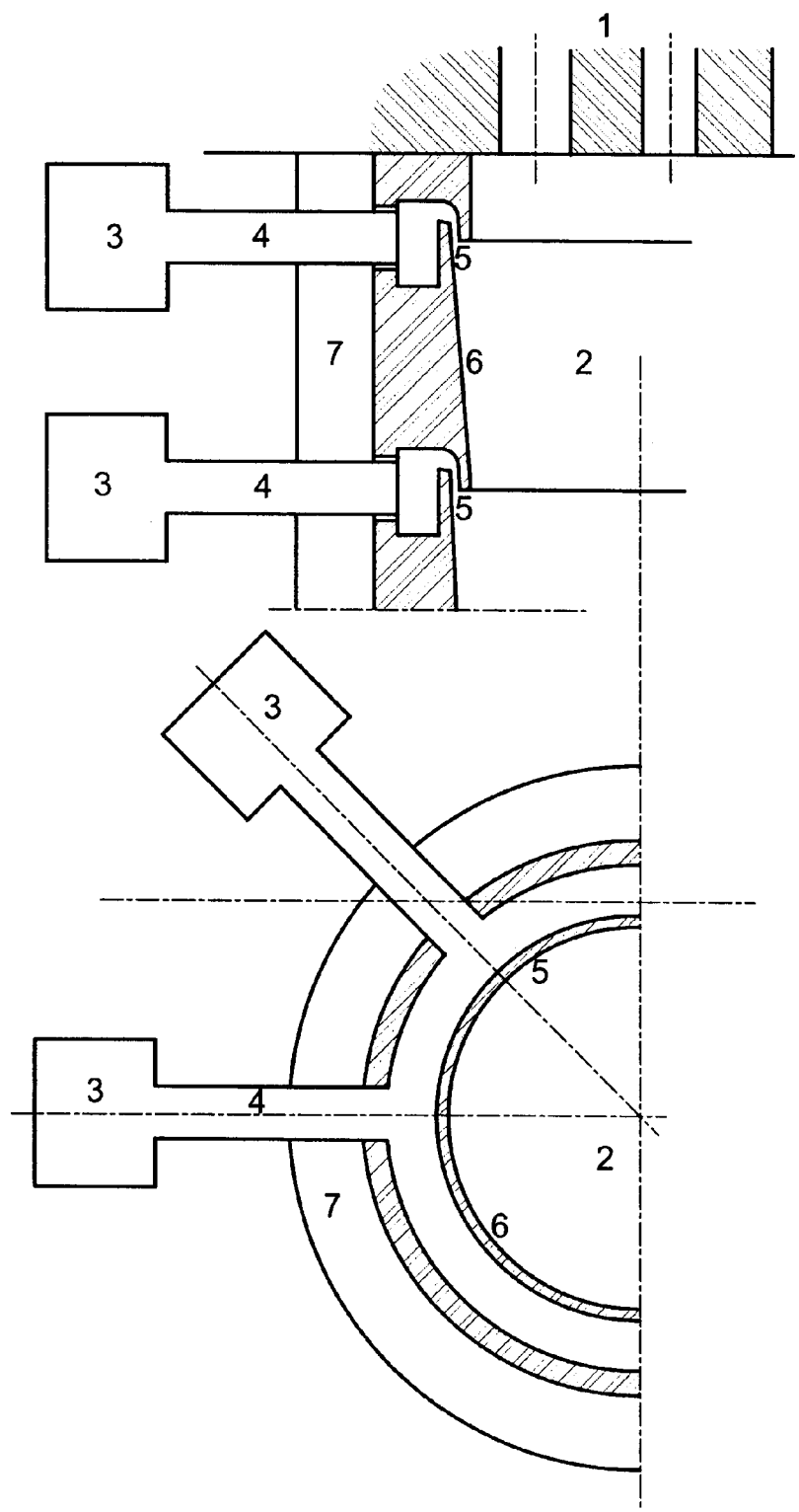
FIG. 2 is two schematic sectional views of the inventive burner.

According to the invention, the exit orifices of the feed lines are in direct proximity to the firing space interior wall to be purged (as shown, for example, in FIG. 2). Preferably, the positioning of the feed lines of the purge gas stream is configured such that the distance of the area centroid of the exit orifice of the feed lines from the firing space interior wall of the combustion space is less than 10 mm, preferably less than 5 mm, more preferably less than 1 mm. The fluid-dynamic boundary layer thickness over the firing space interior wall is calculated, according to the simplified assumption of a flat plate, by the solution of the Blasius boundary layer equation for the distance over the firing space interior wall. Given a distance of 1 to 10 cm, this model gives a boundary layer thickness of 1.5 to 5 mm. For the given geometry properties of the purge apparatus, the result is thus advantageously purging of the boundary layer of the main flow in the firing space. Lack of penetration and crossmixing with the main flow results in a minimized amount of the purge stream required for effective reduction of coking at the wall, which significantly increases the effectiveness of the overall process, since the minimum amount of purge medium, additionally introduced only close to the wall, likewise minimizes the disruptive influence on the time parameters of the POx reactions.

In the process according to the invention, the desired purge principle may, according to the purge medium used, be based on two different mechanisms, both of which may also jointly come into effect, which gives rise to particular synergisms.

The first is pure pulsed, as described above, purging of the flow boundary layer. This leads to avoidance both of the penetration of solid coke/soot particles and the adhesion and growth of soot/coke layers. The velocity of the purge film over the purge surface (firing space interior wall) should preferably be 0.5-1.5 times, more preferably 0.8-1 times, the velocity of the main flow.

Secondly, it is possible for the purge medium to create an oxidizing atmosphere close to the wall, which prevents growth/adhesion of soot/coke by converting/combusting/oxidizing possible impurities with the aid of the oxidizer present in the purge medium, or slows the formation thereof to such an extent that formation of the solid phase is prevented for kinetic reasons.

In the process according to the invention, the purge gas stream is fed in at least two successive sites (each referred to hereinafter as "levels") over the height of the reactor. This likewise minimizes the amount of purge medium to be used, since constantly renewing the purge film close to the wall increases the purge effectiveness. The height of the firing space is understood here to mean, from the alignment, the extent in main flow direction of the gas streams supplied through the burner block. This further enhances the effectiveness of the process, since a dilution of the purge film by the mixing-in of dissociation gas can thus be avoided, and the purge action can thus be ensured over the entire firing space length at low dosage of the purge medium. According to the invention, in a preferred embodiment, the purge flow rate can thus be infinitely adjusted to the coking tendency in the particular firing space section.

Figure 3:
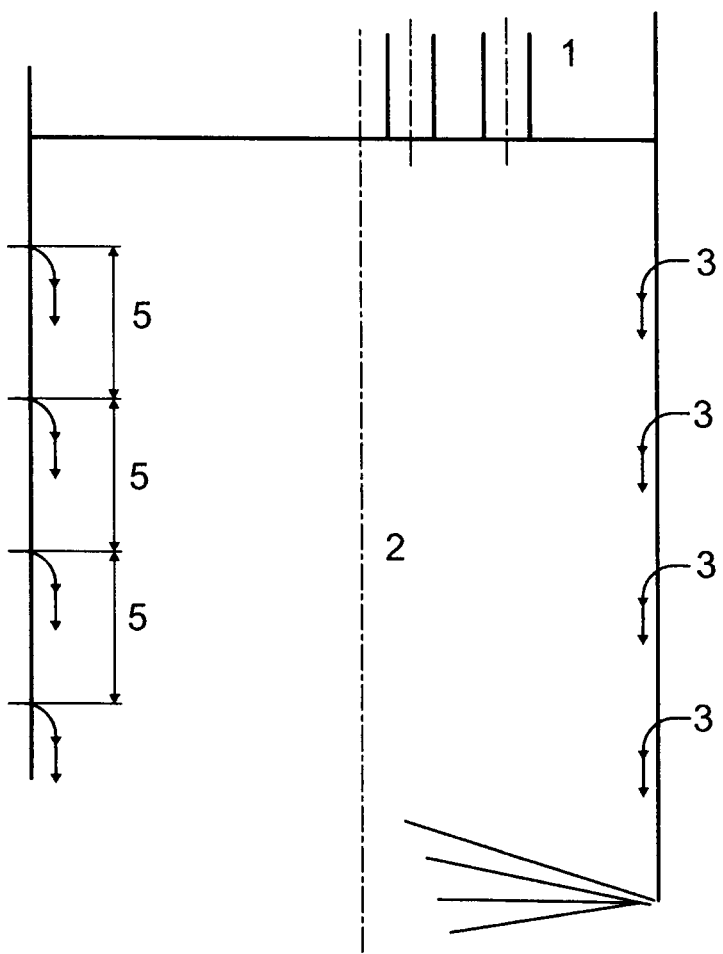
FIG. 3 is a schematic view showing detail of a plurality of feed lines for the purge medium entering the firing space.

One example of such an implementation is shown by way of example in FIG. 3. The distances between the individual feed line stages may be the same or different; they are preferably within a range from 2 cm to 30 cm, more preferably 7 cm to 20 cm. The distance between the individual stages is determined here via the distance between the two exit orifices for the purge medium. Within one level, the feed lines are approximately at one height, more preferably at the same height. FIG. 3 shows the detail of a burner (1) with firing space (2), in the case of which a plurality of feed lines for the purge medium (3) build up a purge film (4) on the firing space interior wall. In addition, the distance (5) between two purge stages (feed line stages) is marked.

It is a further feature of the process according to the invention that, in spite of the multistage addition of the purge gas stream, the firing space diameter is approximately constant, preferably constant, over the height. This ensures constant conditions in the reaction, which is of course, as already outlined above, very sensitive to deviations, and further enhances the effectiveness of the process.

A deviation of the free cross-sectional area resulting from the firing space diameter of less than 10%, based on the maximum free cross-sectional area in the interior of the firing space, can be tolerated here without any lasting impairment of the inventive improvement to such an extent that the positive effect does not predominate, and is considered to be approximately constant in the context of this invention.

According to the invention, any purge medium may be useful for production of the purge pulse, preferably steam. The temperatures of the purge medium are preferably below 500° C., more preferably below 200° C. In this context, the temperatures mentioned relate to the entrance temperature of the purge medium into the firing space. In the case of the above-described oxidative purging action, preferred purge gases for given process technology boundary conditions are potentially oxidizing media, preferably water, steam, oxygen, $CO_2$, CO and mixtures thereof and of further inert components. Preferable in this context are steam, oxygen or mixtures thereof; for example, a particularly advisable purge medium may be one which comprises, as well as predominantly steam, also oxygen within a range of up to 10% by volume.

In a preferred embodiment of the process according to the invention, the surface of the burner block on the firing space side is additionally covered with a purge gas stream. This allows the effectiveness of the process to be enhanced even further, since the coking of this surface can thus also be countered effectively. Suitable purge media are essentially likewise the aforementioned feedstocks.

This invention further provides an apparatus suitable for the performance of the process according to the invention, as shown in FIG. 3, which has already been explained above. It is possible here to discern a customary cylindrical reactor (1) comprising a cylindrical firing space (2) for acetylene preparation, at least two feed lines (3) for a purge gas stream being mounted within the firing space such that the exit orifices of the feed lines are at right angles to the axis of the cylindrical firing space and the exit orifices of the feed lines in the firing space are arranged close to the firing space interior wall, the area centroid of the exit orifices of the feed lines having a distance from the firing space interior wall of less than 10 mm, preferably less than 1 mm.

The process according to the invention makes it possible to prevent encrustations on the firing space interior wall, which can avoid mechanical cleaning operations, for example the use of a stoker unit. It is thus ensured in a lasting manner that no troublesome solid particles of any relevant size get into the gas stream. This makes it possible, in a preferred configuration of the process according to the invention, to recover a large portion of the heat present in the gas after the reaction by means of a downstream heat exchanger. In this case, this energy obtained is preferably used to raise steam. Preferably, a majority of the heat for steam raising can thus be recovered from the product gas produced. Suitable heat exchangers are, for example, shell and tube heat exchangers. Preference is given here to cooling (quenching) the gas stream after the reaction, in contrast to the conventional process, not to 100° C. in the water quench or 200° C. in the oil quench, but rapidly to 600-1000° C. This does not yet lead to any significant yield losses of acetylene as a result of further reactions. Subsequently, this hot product gas is fed to a heat exchanger in which the gas is cooled further. The energy released is used for heat recovery. The heat exchanger is preferably a steam boiler in which the product gas is indirectly cooled further and steam is raised on the secondary side, which can then be used commercially or for operating purposes. This significantly enhances the effectiveness of the process. It is a significant advantage in the configuration of the process according to the invention that the heat exchanger can be connected directly downstream, since no solid deposits lead to problems in this case. In addition to use of the energy released in the cooling of the product gas for steam raising, there are also other opportunities to use this energy in the course of the process for preparing acetylene and synthesis gas.

Such a process regime is not achievable economically in the existing processes, since soot and coke slabs become detached from the firing space interior wall in the course of cleaning in the existing mechanical cleaning processes, are transported in the direction of the heat exchanger and damage it mechanically or abrasively or completely or partially block it. Compared to this, it is possible in accordance with the invention to completely suppress deposition of coke and soot on the firing space interior wall.

The process according to the invention gives an operatively simple and effective means of effectively reducing or even preventing encrustation and baking-on of coke on the firing space interior wall in the preparation of acetylene and/or synthesis gas by partial oxidation. By virtue of the inventive features outlined above, it is already possible here for a relatively small purge gas stream to effectively prevent encrustation, without any lasting impairment of the effectiveness of the reaction. The multi-level configuration of the supply of the purge medium additionally reduces the demand for purge medium, and this advantageously allows the purge medium required to be added in a controlled manner in the individual zones. By appropriate selection of the purge medium, it is possible to create not only a "pure purge operation" based on a pulse of the purge stream, but optionally also preferably an oxidizing atmosphere, which can reduce the deposits further.

EXAMPLES

In the three examples which follow, the comparison between the operation of a burner block/firing space/quench for acetylene synthesis ("standard reactor") according to the prior art and the operation of a reactor according to the invention is to be considered here.

Example 1

The standard reactor was operated for test purposes with conventional axial and radial flame stabilization. The firing space is configured with water cooling.

The reactor diameter with the burners used extends to 180 mm.

The burner block is configured with 19 bores of internal diameter 27 mm in hexagonal arrangement.

The standard reactor and all reactors mentioned hereinafter were operated under these reaction conditions:
natural gas volume flow rate: 600 m³ (STP)/h
ratio of oxygen stream to natural gas stream=0.62
preheating temperature of the gases: 550° C.
acetylene in the volume: 6.4% by volume Under the given test conditions, the standard reactor had to be shut down after approx. 20 operating hours after the occurrence of flame stability problems.

On inspection of the firing space, a coke layer of several centimeters in thickness which had developed on the firing space interior wall can be found in the standard reactor.

The growth rate of the coke layer can be determined to be 4 mm/h.

Example 2

For comparison, an inventive reactor with feed lines for a purge stream in the form of an annular gap having a width of ½₀₀ of the firing space diameter was used. In this example too, the diameter is 180 mm. The purge gas flowed through the feed lines of the purge positions for pulsed purging of the purge boundary layer.

The purge rate was such that the velocity of the purge film was 0.8 times the main flow.

In the course of operation of the inventive reactor, there are no deposits on the firing space interior wall in the firing space over an operating time of 20 h.

The growth rate of the coke layer is accordingly 0.

Example 3

An inventive reactor operated as in example 2 was operated with addition of an oxidizer via the purge positions so as to form an oxidative atmosphere in the purge boundary layer close to the firing space interior wall. In this operation too, deposits are prevented in a lasting manner.

The growth rate of the coke layer here too is 0.

Example 4

An important feature of the process according to the invention is the purging of the firing space interior wall and hence the avoidance of baking-on and coking. The most effective way of accomplishing this in accordance with the invention, as already explained, is by introducing a very thin purge film in the velocity and direction relationship already explained with respect to the main flow into the firing space via feed lines with geometric properties already explained in the course of the description. An important detail of the invention in this context is not to introduce the entire purge stream at one site in the firing space, but to divide the purge stream and supply it to the firing space via a plurality of levels arranged in succession at inventive separations. This leads firstly to an increase in the film effectiveness for the same amount of purge medium introduced in the multi-level variant compared to the one-level variant. Secondly, the same integral film effectiveness can be achieved in multi-level configuration with less purge medium than in the one-level configuration.

The film effectiveness in the context of the invention is defined as follows. It represents the quotient of the concentration difference of the purging medium at the wall (index W) and the main flow (index m) divided by the concentration difference in the purge gas stream (index C) and the main flow (index m):

$$\eta = \frac{C_w - C_m}{C_c - C_m}$$

A calculation model for the film effectiveness based on the purging medium as a function of the axial distance x after the injection of the purge medium is, according to [1]:

$$\eta = A \left\{ \frac{x}{Ms} \left[ Re_c \frac{\mu_c}{\mu_m} \right]^{-0.25} \right\}^{-0.8}$$

According to [1], the constant A represents the experiment-specific geometric and operating boundary conditions.

Figure 4:
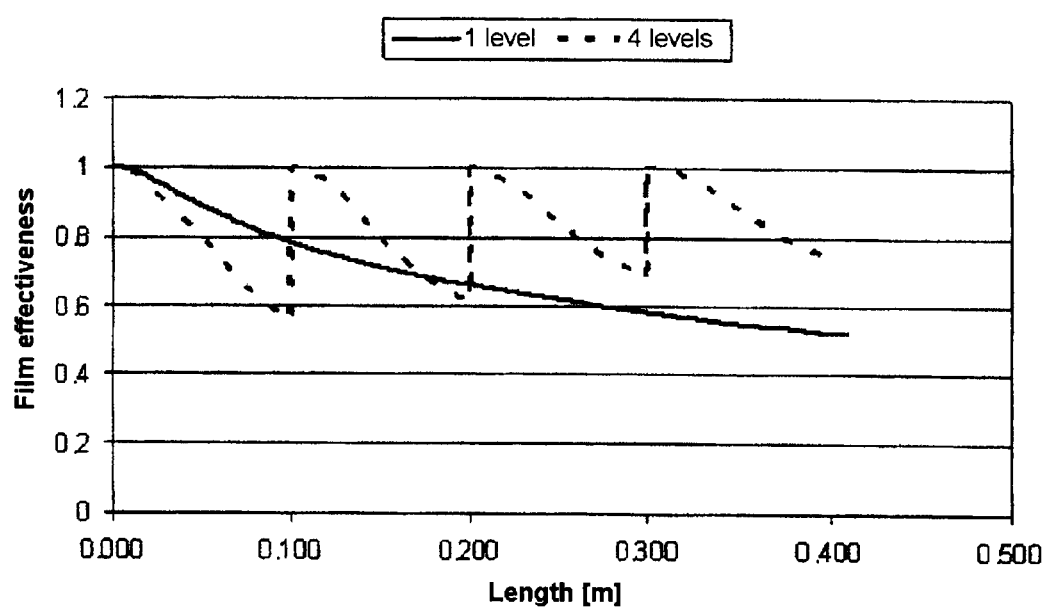
FIG. 4 is a graph plotting effectiveness of the purge film versus length along the firing space, comparing a single-level configuration to a four-level configuration.

In this equation:
M—mass flow ratio
s—opening width
$Re_c$—Reynold number
μ—dynamic viscosity
A—experimental constant
index c—purge film
index m—main flow The table which follows shows, for comparison, the film effectiveness calculated therefrom for a constant total purge stream divided into 4 levels in the inventive case, and divided into only one level in the second case (according to the prior art). This shows the inventive advantages of multi-level purging. Accordingly, for the inventive four-level variant, an increase in the integral film effectiveness averaged over the firing space surface area of 20% is found compared to the one-level variant with the same total purge flow introduced into the firing space. FIG. 4 shows a graphic comparison of the two film effectiveness. The film effectiveness is plotted here over the length (in m). The continuous line represents the case of one level, the broken line the inventive case of four levels.

The simulation software used was ANSYS FLUENT Flow Modeling Software Version 6.3.

[2] Burns, W. K. and Stollery, J. L., The influence of foreign gas injection and slot geometry on film cooling effectiveness, Int. J. Heat Mass Transfer, Vol. 12, p. 935-951

TABLE

Example - comparison of one- and four-level purging of the firing space interior wall
Mass flow rate: 0.052 kg/s
injected via one and four levels

| Length [m] | Film effectiveness 1 level | Film effectiveness 4 levels |
|---|---|---|
| 0.00 | 1 | 1 |
| 0.05 | 0.88683844 | 0.739 |
| 0.10 | 0.777158774 | 0.544 |
| 0.10 | 0.777158774 | 1 |
| 0.15 | 0.715233613 | 0.798 |
| 0.20 | 0.662728085 | 0.64 |
| 0.20 | 0.662728085 | 1 |
| 0.25 | 0.584392286 | 0.84 |
| 0.30 | 0.584392286 | 0.702 |
| 0.30 | 0.584392286 | 1 |
| 0.35 | 0.549715748 | 0.861 |
| 0.40 | 0.523118006 | 0.744 |

For one level, the integral mean is η=0.69; for four levels, the integral mean is η=0.83; this corresponds to an increase of approx. 20%.

The invention claimed is:

1. A process for preparing acetylene and synthesis gas by partial oxidation of at least one hydrocarbon with oxygen, by first separately preheating the starting gases comprising a hydrocarbon-comprising stream and an oxygen-comprising stream and then mixing them in a mixing zone and, after they have flowed through a burner block, reacting them in a firing space and then cooling the products rapidly, wherein the firing space interior wall is blanketed with a purge gas stream, this purge gas stream is introduced by means of a plurality of feed lines and each of these feed lines is configured in the interior of the firing space such that the alignment of the direction vector of the main flow of the purge gas stream introduced deviates from the alignment of the direction vector of the main flow direction of the gas stream supplied through the burner block by an angle of not more than 10°, and the feed lines at the exit orifice thereof have an opening width of $1/1000$ to $3/100$, of the firing space diameter, there being a multi-level supply of the purge gas stream at successive points viewed in relation to the main flow direction of the gas stream supplied through the burner block, and the free cross section of the firing space which is available to the gas stream leaving the burner block for flow through the firing space at the height of the feed lines of the purge gas stream being approximately constant.

2. The process according to claim 1, wherein the direction vectors of the main flow directions of purge gas stream and of the gas stream supplied through the burner block to the firing space are parallel.

3. The process according to claim 1, wherein the purge gas stream is supplied to the cylindrically shaped firing space in homogeneous distribution over the periphery in such a way that the purge gas stream is introduced with one to eight feed lines.

4. The process according to claim 3, wherein the exit orifices of the feed lines of one level are arranged at the same height within the firing space.

5. The process according to claim 4, wherein the purge stream is fed in over the height of the firing space by means of a plurality of feed line levels according to claim 4, the distance between the individual feed line levels being 2 cm to 30 cm.

6. The process according to claim 5, wherein the distance between the individual feed line levels are 7 cm to 20 cm.

7. The process according to claim 1, wherein the exit orifices of the feed lines of the purge stream are circular, rectangular or square, or form an annular gap surrounding the circumference of the firing space.

8. The process according to claim 1, wherein the purge medium used is steam, oxygen or a mixture thereof.

9. The process according to claim 1, wherein the purge medium comprises up to 10% by volume of oxygen.

10. The process according to claim 1, wherein the area centroid of the exit orifices of the feed lines has a distance from the firing space interior wall of less than 10 mm.

11. The process according to claim 1, wherein the gas, after the reaction in the firing space, is cooled to a temperature of 600 to 1000° C. and then supplied to a heat exchanger in which the gas is cooled further, and the energy released is used for heat recovery.

12. The process according to claim 1, wherein the area centroid of the exit orifices of the feed lines has a distance from the firing space interior wall of less than 1 mm.

* * * * *